United States Patent [19]
Henley

[11] Patent Number: 5,331,979
[45] Date of Patent: Jul. 26, 1994

[54] IONTOPHORETIC CIGARETTE SUBSTITUTE

[76] Inventor: Julian L. Henley, 38 Munger Rd., Guilford, Conn. 06437

[21] Appl. No.: 919,261

[22] Filed: Jul. 27, 1992

[51] Int. Cl.⁵ .............................................. A24F 47/00
[52] U.S. Cl. ...................................... 131/273; 131/359; 604/20
[58] Field of Search ................. 131/270, 273, 359; 604/20

[56] References Cited

U.S. PATENT DOCUMENTS

| | | | |
|---|---|---|---|
| 4,211,222 | 7/1980 | Tapper | 128/803 X |
| 4,393,884 | 7/1983 | Jacobs | 131/273 |
| 4,416,274 | 11/1983 | Jacobsen et al. | 128/803 X |
| 4,429,703 | 2/1984 | Haber | 131/273 |
| 4,655,229 | 4/1987 | Sensabaugh, Jr. et al. | 131/273 |
| 4,708,716 | 11/1987 | Sibalis | 604/20 |
| 4,735,217 | 4/1988 | Gerth et al. | 131/273 |
| 4,756,318 | 7/1988 | Clearman et al. | 131/359 |
| 4,771,796 | 9/1988 | Myer | 131/273 |
| 4,776,353 | 10/1988 | Lilja et al. | 131/297 |
| 4,793,366 | 12/1988 | Hill | 131/273 |
| 4,800,903 | 1/1989 | Ray et al. | 131/273 |
| 4,813,437 | 3/1989 | Ray | 131/273 |
| 4,907,606 | 3/1990 | Lilja et al. | 131/273 |
| 4,917,119 | 4/1990 | Potter et al. | 131/273 |
| 4,922,901 | 5/1990 | Brooks et al. | 128/203.26 |
| 4,950,229 | 8/1990 | Saje, Jr. | 604/20 |
| 5,060,671 | 10/1991 | Counts et al. | 131/329 |
| 5,160,316 | 11/1992 | Henley | 604/20 |
| 5,167,242 | 12/1992 | Turner et al. | 131/273 |

Primary Examiner—William H. Grieb
Attorney, Agent, or Firm—Ralph D'Alessandro

[57] ABSTRACT

An improved iontophoretic cigarette substitute device is disclosed having a driver unit and a disposable mouthpiece. The mouthpiece has a drug coating applied to its external surface which is iontophoretically driven into the mucous membranes of the user's lips upon use. Nicotine is a preferred drug to be administered to the user through an electrode employed on the mouthpiece.

9 Claims, 1 Drawing Sheet

IONTOPHORETIC CIGARETTE SUBSTITUTE

FIELD OF THE INVENTION

This invention relates generally to a smokeless cigarette and, more specifically, to a smokeless iontophoretic cigarette that employs a replaceable mouthpiece from which nicotine is delivered through the mucous membranes of the mouth and the lips to the user.

BACKGROUND OF THE INVENTION

Since cigarette smoking has long been suspected and has now been determined to be potentially harmful to the health of humans, numerous alternative cigarette substitute designs have been developed in order to provide a safe alternative and still satiate the habits associated with cigarette smoking. These habits include the addictive properties of nicotine, the hand-mouth or finger-mouth habit, and the taste and smell associated with tobacco. Alternative designs have attempted to avoid the deleterious substances formed during the combustion of tobacco, including carbon monoxide, tar products, aldhydes and hydrocyanic acid.

Numerous products have been produced to attempt to satisfy the nicotine addiction or dependence of tobacco smokers. One such product is chewing gum that provides nicotine at the time of need in an attempt to remove the withdrawal effects from nicotine when a smoker stops. This has been moderately successful in helping smokers break the smoking habit. Another approach employs a nicotine patch whereby nicotine is delivered by the nicotine impregnated patch via a percutaneous passive system. This approach, however, delivers a relatively low level of nicotine estimated to be about 21 milligrams per 24 hours. This also has been only moderately successful in helping individuals break the smoking habit. Both of these approaches also suffer from the deficiency of not satisfying the aforementioned hand-mouth or finger-mouth habit.

Other approaches have utilized pyrolitic and non-pyrolytic methods of delivering drugs, including nicotine vapors, to the user upon demand created by the user's sucking on a mouthpiece of the delivery device. The nonpyrolytic devices include nicotine bearing fibers or filters within cigarette-shaped dispensers that utilize air drawn through by the user to release the drug vapors or entrain powdery particulate matter. Other devices utilize some type of a heating element, such as an electrical resistance heater to vaporize or otherwise release the drug vapors in aerosol form. All of these devices deliver nicotine to the lung and depend upon the passive absorption of the drug into the blood stream. the safety and the efficacy of these systems have not been established.

The commercial gum product available allows a passive absorption of nicotine through mucous membranes when the user chews. However, none of these are effective to permit concentrated supply of the drug by driving the drug, such as nicotine, through the user's membranes quickly and effectively into the user's system.

These problems are solved in the design of the present invention by providing a smokeless iontophoretic cigarette substitute that employs a removable and replaceable mouthpiece that is coated with a nicotine-containing coating that is iontophoretically driven through the mucous membranes of the user's lips into the user's system. The present invention utilizes the efficacy of mucous membrane absorption by actively iontophoretically driving the nicotine through the mucous membrane of the lips, thereby completely bypassing the potentially harmful exposure of the lungs to smoke or other inhalants.

SUMMARY OF THE INVENTION

It is an object of the present invention to provide an iontophoretic smokeless cigarette substitute that satisfies all of the habits which accompany cigarette smoking.

It is another object of the present invention to provide a smokeless cigarette substitute that avoids the carcinogenic components of tobacco.

It is a feature of the present invention that the smokeless iontophoretic cigarette substitute utilizes a two piece design including a disposable mouthpiece and a reuseable driver unit.

It is another feature of the present invention that the disposable mouthpiece has an electrode design on its surface to permit the nicotine containing substance to be iontophoretically driven into the user's system.

It is still another feature of the present invention that the power source to electrically drive the nicotine and the electronics associated with that power source are included in the reuseable driver unit to which is detachably connected the mouthpiece.

It is yet another feature of the present invention that the disposable mouthpiece is connected to the driver unit so that the circuit pattern on the mouthpiece is positioned against electrical contacts on the driver unit.

It is yet a further feature of the present invention that the mouthpiece is hollow and has vents to permit the user to suck air therethrough to satisfy the sucking habit present in smoking.

It is still a further feature of the present invention that the hollow mouthpiece can have some tobacco on its inner wall to release a tobacco aroma.

It is an advantage of the present invention that the design will satisfy the hand-mouth or finger-mouth sucking habit.

It is another advantage of the present invention that the design will provide the delivery of nicotine to the user in a dynamic fashion upon demand by the user.

It is still another advantage of the present invention that the design will permit the aroma of tobacco to be present for the user.

It is yet another advantage of the present invention that the design will satisfy the habits of a smoker without combustion or delivering the carcinogenic or other harmful tobacco combustion by-products to the lungs.

These and other objects, features and advantages are obtained by the smokeless iontophoretic cigarette substitute which employs a disposable hollow mouthpiece that has circuit pattern on its outer surface and is coated with a nicotine-containing coating which has the nicotine driven into the mucous membranes of the lips by the electronic driving assembly contained within the reusable driving unit.

BRIEF DESCRIPTION OF THE DRAWINGS

The objects, features and advantages of the invention will become apparent upon consideration of the following detailed disclosure of the invention, especially when it is taken in conjunction with the accompanying drawings wherein.

DETAILED DESCRIPTION OF THE PREFERRED EMBODIMENT

It is to be understood that although the present invention is intended to be used for the delivery of nicotine or a nicotine substitute drug in a smokeless iontophoretic cigarette, it can equally well be used to deliver any suitable drug or medicament that is desired to be administered to a user or patient through the mucous membranes of the lips.

Figure 1:
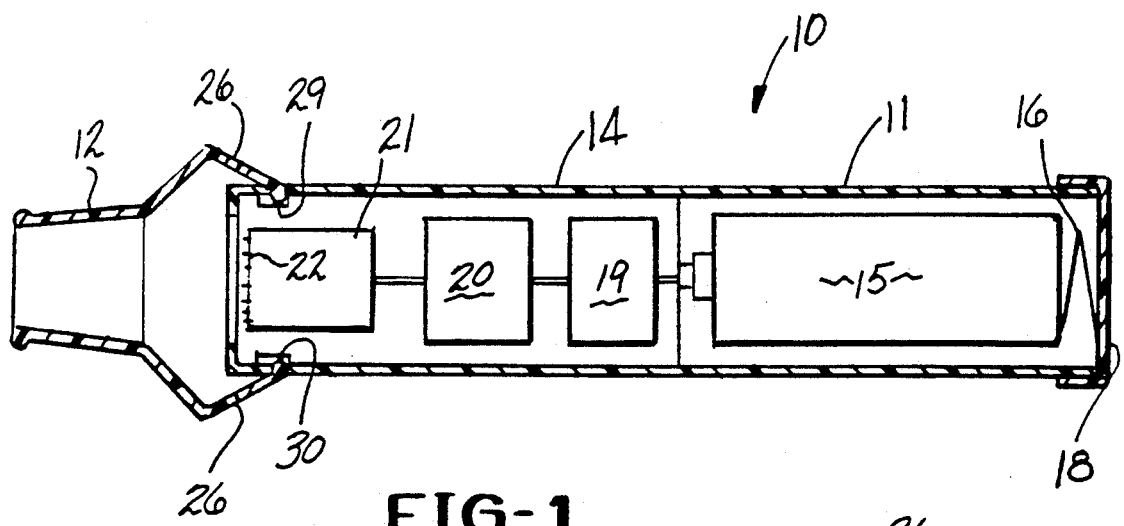
FIG. 1 is a top sectional diagrammatic illustration of the smokeless iontophoretic cigarette showing the driving unit and its electronics with the detachable mouthpiece connected thereto.
Figure 2:
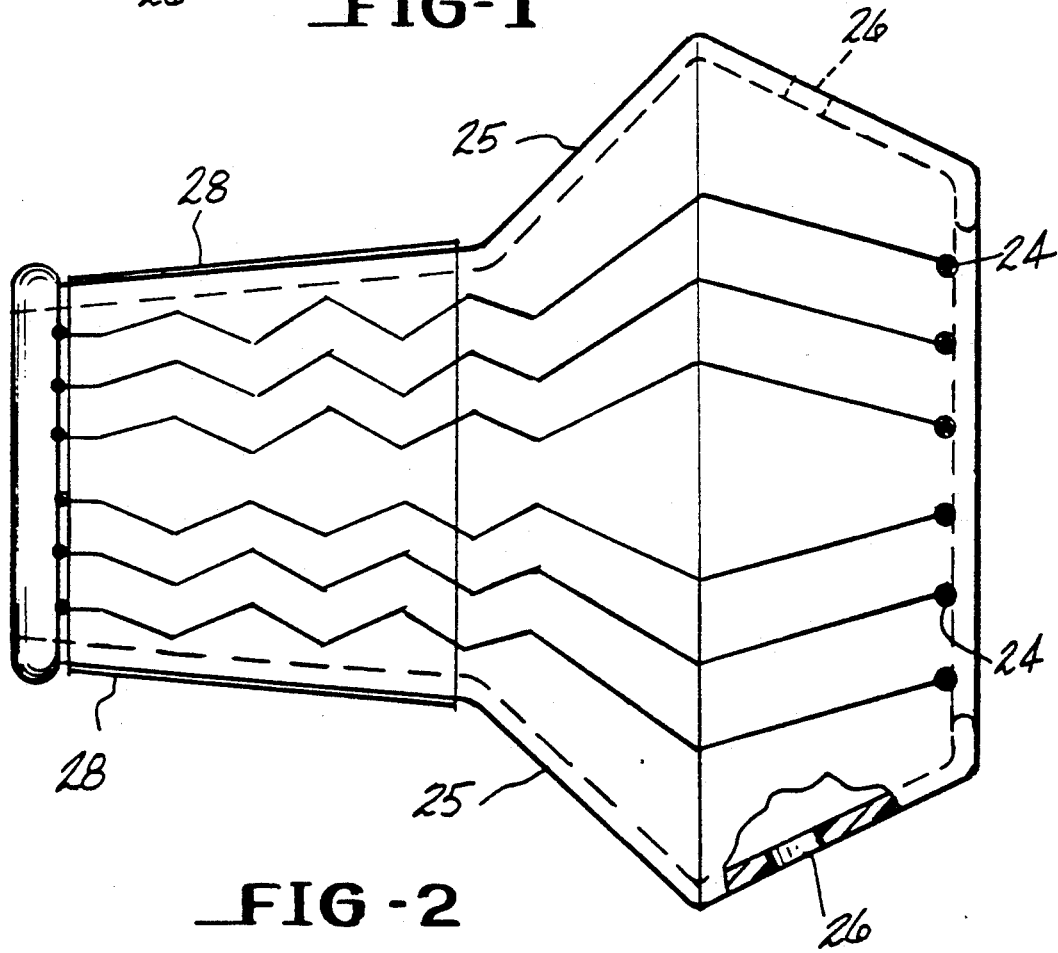
FIG. 2 is an enlarged diagrammatic illustration of one potential embodiment of the disposable mouthpiece showing the circuit pattern and the nicotine-containing coating thereon.

As seen in FIG. 1, the cigarette substitute device 10 consists of two main sections; a driver unit 11 and a hollow mouthpiece 12. The driver unit is contained within a tubular or cylindrically shaped housing 14 that may be formed of any appropriate material, such as plastic. Driver unit 11 is intended to be reuseable, so that it must be sufficiently durable in construction to permit replacement of the battery 15 through the removable end cap 18. End cap 18 has a spring 16 which can be used to force the negative end of the battery forward so that the positive end touches the contact 17 to complete the circuit to permit the stored electrical energy to be supplied to drive the iontophoretic device 10. Driver unit 11 also contains a voltage multiplier 19 which permits sufficient voltage to be supplied to current driver 20 so that sufficient current is sent through distribution circuit 21 and its electrical contacts 22 to permit the medicament present in the coating 28 of mouthpiece 12 to be driven into the mucous membranes of the lips of the user by means of a plurality of surface electrodes. When the device 10 is not in use, the end cap 18 is loosened so that the electrical circuit is broken and no current flows through distribution circuit 21 to the mouthpiece 12.

Housing 14 of driver unit 11 has an active electrode 29 and a passive electrode 30 in its sidewalls connected to the distribution circuit 21 to permit current to be supplied to the disposable mouthpiece 12 with its iontophoretic circuit pattern 24 and medicament coating 28. The mouthpiece 12 has a multichannel electrodispersive matrix or circuit pattern 24 to drive the ionic medicament from the surface of the mouthpiece 12 into the skin area or mucous membranes of the lips of the user. The medicament is preferably a hardened polygel from any suitable one of the hydrogels that are characterized by having an adhesive component so it remains on the outer surface of the mouthpiece 12, is conductive, and provides good tissue contact. The gel must also be impregnable with medicament or suitable drug, which in the preferred instance of the present invention is a nicotine or nicotine substitute drug. A gel that is rubberlike in consistency is desirable.

The iontophoretic medicator or mouthpiece 12 has a plurality of electrode lead wires that lead from the positive or active electrode connection 29 and the negative or ground electrode connection 30. These lead wires connect to the plurality of electrodes on the mouthpiece 12; the active ones are on the top surface of the mouthpiece 12, preferably etched thereon, and contains or contacts the ionic agent or medicament in the coating 28 to be administered to the user and the other which is the electric current distribution conductive member or grounding electrode (not shown) which is present on the opposing side of the mouthpiece 12. These grounding electrodes (not shown) must also cover an area similarly large in size to the area covered by circuit pattern or electrodes 24.

Together these electrodes form a closed circuit through the user's body when current is applied to promote the penetration or absorption of the ionic layer contained in the medicament in the coating 28 that is in contact with the working electrode 24. The polarity of the working electrode 24 is selected based upon the polarity of the medicament to be administered. The working electrode 24 will be described in greater detail hereafter. The current distributing working electrode 24 can be a flexible sheet or film with a current distribution conductive member or layer, such as a metallic foil, for example aluminum or other suitable metals, a conductive rubber or resin film, carbon film or other conductive coating.

A suitable connector (not shown) connects the electrical power source to the circuit pattern 24 and delivers the electrical current via the connectors 23 to the lead wires that form the individual electrically conductive channels 27 in the conductive matrix formed by the electrodes of circuit pattern 24. The mouthpiece 12 slides over the housing 14 of the the driver unit 11 so that the electrode contacts 23 fit over and contact the electrode contacts 22 of the distribution circuit 21 since the material of construction is flexible, to permit a good electrical connection to be made between the connectors. Each channel or lead wire 27 preferably carries no more than 0.6 milliamps. The amount of current that flows to each channel is controlled by the current driver 20 and the distribution circuitry 21 to prevent a tunneling effect from occurring. This prevents the flow of current along the path of least resistance through a lesion or skin rupture, for example, on the lips of the user that could result in a burn to the user at that location. The multichannel electrode of the circuit pattern 24 can be etched onto the surface of the disposable mouthpiece 12, such as by laser or photoetching. The receiving surface of the mouthpiece 12 can, for example, be a Mylar ® plastic on a suitable supporting substrate, such as polyethylene or polypropylene plastic. Each channel 27 of electrodes 24 is isolated to obtain the desired wide area dispersion through the mucous membranes of the lips of the user. The connectors 23 will scrape off upon removal from the driver unit 11 with the power source to prevent reuse.

Each channel formed by the lead wires or channels 27 of circuit pattern 24 can be electrically driven simultaneously or in a sequential multiplex fashion. The simultaneous or parallel electrical current use is preferred to achieve a wide area dispersion across the lips of the user.

The disposable mouthpiece 12 of the present invention with the medicament coating 28 applied possesses the advantages of not suffering from a leaching out of the medicament from a rupturable polymer reservoir, no attendant loss of efficacy, a long shelf life and little or no electrode corrosion. Mouthpiece 12 also possesses at least a pair of side vents 26 to permit air to be drawn through the mouthpiece of the cigarette substitute device to simulate the sucking that accompanies the smoking habit.

If desired, the inner surface of the hollow mouthpiece 12 can be lined with a tobacco extract or tobacco "raisins" to provide the aroma and taste of tobacco to the user of the cigarette substitute 10.

The battery 15, which is preferably a AAA sized battery, is connected to the voltage multiplier 19 that may be in the form of a micro-chip which is sufficient to provide voltage in the range of 18-28 volts to the mouthpiece in order to obtain good iontophoretic penetration of the drug. The current driver 20 comprises limited circuits that can be placed in a custom-made chip. The distribution circuit drives the current in a limited fashion to the electrodes used so that the mouthpiece 12, with its circuit pattern 24 that is photoetched or embedded thereon, can deliver the drug to the user in the desired range. In the case of nicotine, this will be in the range of about 2 to about 10 milligrams.

The multichannel electrode is explained in further detail in copending application Ser. No. 07/579,799 filed Sept. 9, 1990, now U.S. Pat. No. 5,160,316 and is hereby specifically incorporated by reference in pertinent part insofar as it is consistent with the present invention.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. An iontophoretic drug delivery device comprising in combination:
   (a) a first driver unit comprising an electrical power source; and
   (b) a second mouthpiece unit detachably connectable to the driver unit having an external surface, the external surface having electrodes thereon and a coating containing the drug to be delivered to a user of the device.

2. The drug delivery device according to claim 1 further comprising the mouthpiece unit being hollow and having vents therein to permit the user to draw air therethrough.

3. The drug delivery device according to claim 1 further comprising first driver having a voltage multiplier.

4. The drug delivery device according to claim 3 further comprising first driver having a current limited distributor connected to the voltage multiplier.

5. The drug delivery device according to claim 4 further comprising first driver having a current limited distribution circuit connected to the current limited distributor.

6. The drug delivery device according to claim 5 further comprising the source of electrical power comprising a battery connected to the voltage multiplier.

7. The drug delivery device according to claim 1 further comprising the electrode comprising a circuit pattern etched onto the surface of the mouthpiece.

8. The drug delivery device according to claim 1 further comprising the coating being a gel.

9. The drug delivery device according to claim 8 further comprising the drug contained within the gel being nicotine.

* * * * *